United States Patent [19]

Dancer et al.

[11] Patent Number: 5,299,254
[45] Date of Patent: Mar. 29, 1994

[54] METHOD AND APPARATUS FOR DETERMINING THE POSITION OF A TARGET RELATIVE TO A REFERENCE OF KNOWN CO-ORDINATES AND WITHOUT A PRIORI KNOWLEDGE OF THE POSITION OF A SOURCE OF RADIATION

[75] Inventors: Paul Dancer, Saint-Etienne; Francois Lacoste, Lyon, both of France

[73] Assignee: Technomed International, Paris, France

[21] Appl. No.: 963,010

[22] Filed: Oct. 19, 1992

Related U.S. Application Data

[63] Continuation of Ser. No. 615,449, Nov. 19, 1990.

[30] Foreign Application Priority Data

Nov. 24, 1989 [FR] France .................... 89 15515
Aug. 6, 1990 [FR] France .................... 90 10040

[51] Int. Cl.$^5$ ................................... H05G 1/28
[52] U.S. Cl. ........................... 378/163; 128/653.1; 378/162
[58] Field of Search .................... 378/162, 163; 128/653.1

[56] References Cited

U.S. PATENT DOCUMENTS

| | | | |
|---|---|---|---|
| 2,474,422 | 6/1949 | Hollsteen | 378/206 |
| 3,577,160 | 5/1971 | White | 378/162 |
| 3,717,768 | 2/1973 | Edholm et al. | 250/86 |
| 4,727,565 | 2/1988 | Ericson | 378/163 |
| 4,750,487 | 6/1988 | Zanetti | 378/162 |
| 4,764,944 | 8/1988 | Finlayson | 378/20 |
| 4,819,257 | 4/1989 | Grasser et al. | 378/99 |
| 5,070,861 | 12/1991 | Einars et al. | 378/162 |

FOREIGN PATENT DOCUMENTS

| | | |
|---|---|---|
| 2909476 | 9/1980 | Fed. Rep. of Germany . |
| 3904595 | 4/1990 | Fed. Rep. of Germany . |
| 3919083 | 6/1990 | Fed. Rep. of Germany . |

Primary Examiner—Craig E. Church
Attorney, Agent, or Firm—Cohen, Pontani, Lieberman & Pavane

[57] ABSTRACT

The invention relates to a method and to apparatus determining the exact position of a target relative to a reference of known co-ordinates. The apparatus comprises a source of radiation for forming an image of a target, which image is received by a receiver device situated beyond the target. A mask-forming device is interposed between the receiver device and the source of radiation, the mask-forming device including at least one localization means of known position relative to a reference point and suitable for forming an image in said image-forming radiation, means are also provided for displacing the radiation source in three dimensions, at least between two different angular positions, thereby displacing the co-ordinates of two different images of the target obtained from the two different angular positions of the source. The invention makes it possible to determine the exact position of a target with a very high degree of precision using a method which is simple and which limits the radiation dose. The target may be a cell or a stone or a bone to be treated.

53 Claims, 5 Drawing Sheets

Fig-3

METHOD AND APPARATUS FOR DETERMINING THE POSITION OF A TARGET RELATIVE TO A REFERENCE OF KNOWN CO-ORDINATES AND WITHOUT A PRIORI KNOWLEDGE OF THE POSITION OF A SOURCE OF RADIATION

This is a continuation of application Ser. No. 07/615,449, filed Nov. 19, 1990.

The present invention relates essentially to a method and to apparatus for determining the position of a target relative to a reference of known co-ordinates and without a priori knowledge of the position of a source of radiation.

BACKGROUND OF THE INVENTION

Various methods and apparatuses are already known for determining the exact position of a target by using a source of radiation emitting radiation which can be received by a receiver device, the said source and said receiver device being disposed on opposite sides of said target (see EP-A-0 242 565 or EP-A-0 260 550).

In prior apparatuses, the source of radiation is exclusively a source of X-rays, thereby tending to subject a patient to considerable doses of X-ray irradiation, which is not desirable.

Further, prior methods and apparatuses require the X-ray source and the radiation receiver device to be fully integrated with equipment for treating the target, which means that radiation sources that may already exist in treatment centers are unsuitable, thereby considerably increasing the cost of such apparatuses.

Another major drawback of prior methods and apparatuses lies in the fact that they require the initial position of the source to be known, which is why they need to be fully integrated in the target treatment equipment.

Thus a main object of the present invention is to solve the novel technical problem consisting in determining the exact position of a target independently of a priori knowledge of the position in three dimensions of the source of radiation.

Another main object of the present invention is to solve the novel technical problem consisting in providing a method and an apparatus for determining the exact position of a target without a priori knowledge of the distance and/or angular position in three dimensions of the source of radiation relative to said target, the apparatus being simple in design and cheap.

Another object of the present invention is to solve the novel technical problem consisting in providing a method and apparatus for determining the exact position of a target independently of a priori knowledge of the position in three dimensions of the source of radiation making use of a source of radiation which is independent of the target treatment equipment, which is particularly advantageous for therapeutic treatment of targets that may be constituted, for example, by cells, lithiases or concretions, or bones to be treated. The invention also makes it possible to use sources of radiation that are available in treatment centers for other purposes.

Another object of the present invention is to solve the novel technical problems specified above with a minimum of manipulation, in particular using a minimum number of steps or taking a minimum number of pictures with the localization apparatus, thus limiting the dose of exposure to the radiation emitted by the localization apparatus, which is particularly important when the localization apparatus emits X-rays.

Another object of the present invention is to solve the novel technical problem consisting in determining the exact position of a target without having to displace the patient.

For the first time, the present invention makes it possible to solve the technical problems specified above simultaneously, particularly simply, cheaply, and in a manner that is usable on an industrial scale.

SUMMARY OF THE INVENTION

Thus, in a first aspect, the present invention provides a method of determining the exact position of a target relative to a reference point as determined, for example, by means of equipment for treating the target, the method comprising the steps of using an emission device comprising a radiation source for emitting image-forming radiation for forming an image at least of the target and capable of being received by a receiver device for receiving said radiation, said source and said receiver device being disposed on opposite sides of said target, wherein:

a mask-forming device is disposed between said receiver device and said radiation source, the mask-forming device comprising at least one localization means of known position relative to said reference point, said localization means being suitable for forming an image using said image-forming radiation;

the emission device is brought into a position facing a localization means;

the radiation source is adjusted approximately into a first angular position in three dimensions relative to the localization means, and it is verified that said radiation simultaneously encompasses the receiver device, the target, and the localization means;

said source is caused to emit said image-forming radiation in order to form a first image of the target and a first image of said localization means on the receiver device, and the respective first position co-ordinates thereof are noted;

the radiation emission device is displaced to an angular position which is different from the preceding angular position, and being capable, in said different angular position, of simultaneously encompassing the receiver device, the target, and the localization means;

the radiation source is adjusted approximately into a second angular position in three dimensions relative to the localization means, and it is verified that said radiation simultaneously encompasses the receiver device, the target, and the localization means;

said source is caused to emit second radiation to obtain a second image of the target, and a second image of said localization means on the receiver device, and the respective second position co-ordinates thereof are noted; and the co-ordinates of the target are calculated from the known co-ordinates of the localization means and on the basis of at least some of the co-ordinates of the first and second images of the target, and of at least some of the co-ordinates of the first and second images of said localization means.

In a preferred implementation of the invention, the invention provides a method of determining the exact position of a target relative to a reference point as determined, for example, by equipment for treating the target, the method comprising using an emission device comprising a radiation source emitting image-forming radiation for forming an image at least of the target and capable of being received by a receiver device for receiving said radiation, said source and said receiver device being disposed on either side of the target and wherein:

a mask-forming device is interposed between said receiver device and said source of radiation whose position is unknown, the mask-forming device comprising at least two groups of localization means having known positions relative to the reference point, i.e. a first group of localization means and a second group of localization means, said first and second groups of localization means being disposed at two different known angular orientations relative to the reference point, said first group and said second group of localization means being suitable for forming images by means of said image-forming radiation;

the emission device is brought to a first position facing the first group of localization means;

the radiation source is adjusted approximately into a first angular position in three dimensions relative to the first localization means and it is verified that the said radiation simultaneously encompasses the receiver device, the target, and the first group of localization means;

the source is caused to emit image-forming radiation in order to obtain a first image of the target and a first image of the first group of localization means on the receiver device, and the respective first position co-ordinates thereof are noted;

the radiation emission device is displaced to face the second group of localization means;

the radiation source is approximately adjusted into a second angular position in three dimensions relative to the second group of localization means, and it is verified that said radiation simultaneously encompasses the receiver device, the target, and the second group of localization means;

the source is caused to emit image-forming radiation to form a second image of the target and a second image of the second group of localization means on the receiver device, and the respective second position co-ordinates thereof are noted; and the co-ordinates of the target are calculated on the basis of the known co-ordinates of the first and second groups of localization means, on the basis of at least some of the co-ordinates of the first image of the target, on the basis of at least some of the co-ordinates of the second image of the target, and on the basis of at least some of the co-ordinates of the images of the first and second groups of localization means.

In a variant implementation, a first group of at least three localization means is provided disposed in a given plane and having known co-ordinates, together with a second group of at least three localization means of known co-ordinates disposed in a common oblique plane sloping at a known angle relative to the first group of localization means.

In a variant implementation, one of the localization means is disposed on the axis of symmetry of the target treatment equipment with the reference point likewise lying on said axis.

In another variant implementation, the plane of the first group of localization means is disposed substantially perpendicular to the axis of symmetry of the treatment equipment.

In another particular variant implementation of the method of the invention, at least one shadow means is disposed between the target and the receiver device to form a shadow, e.g. a cross, on the receiver device while the radiation for forming an image of the target is being emitted, the co-ordinates of said shadow means being known relative to the reference point.

In another variant implementation, a group is provided comprising a plurality of shadow means (preferably three), with at least some of the shadow means being disposed on the opposite side of the axis of symmetry of the treatment equipment relative at least to the first group of localization means.

In yet another particular variant implementation of the invention, a first group of at least three reference means is provided having co-ordinates that are known relative to the reference point, a first reference means being disposed on an axis of symmetry of the target treatment equipment passing through the reference point, a second reference means being disposed on an X-axis defined by the longitudinal displacement axis of the treatment equipment, and a third reference means disposed on an Y-axis defined by the transverse displacement axis of the target treatment equipment.

In yet another particular variant implementation of the method of the invention, a group of at least three shadow means is provided, disposed between the target and the receiver device, said shadow means being preferably disposed in the vicinity of the receiver device and forming a shadow, e.g. a cross, on the receiver device while the radiation for forming an image of the target is being emitted. The co-ordinates of the shadow means being known relative to the reference point, the group comprising a first shadow means disposed on an axis of symmetry of the target treatment equipment so that its shadow on the receiver device preferably defines the above-mentioned reference point, a second shadow means disposed in a plane defined by the axis of symmetry of the target treatment equipment and the substantially longitudinal displacement direction of the target treatment equipment, which direction is referred to as the positive X-axis, and a third shadow means disposed in the plane defined by the Z-axis of symmetry of the target treatment equipment and by the direction substantially transverse to the displacement direction of the target treatment equipment, said direction being referred to as the positive Y-axis.

In a particular variant implementation of the invention, the image-forming radiation source is an X-ray source and the receiver device includes an X-ray sensitive film, the method preferably including a system for measuring cartesian co-ordinates, e.g. in the form of a digitizing tablet.

In another variant implementation of the invention, the image-forming radiation source is an X-ray source and the receiver device comprises a fluoroscopic receiver device, preferably fitted with a monitor screen provided with a system for measuring cartesian co-ordinates, the system for measuring cartesian co-ordinates being integrated or independent, e.g. in the form of a system for digitizing a video signal.

In a variant implementation, the radiation-emitting device also includes means for emitting collimation radiation which is preferably visible, thereby facilitating alignment of the emission device on the reference means.

In a particular variant implementation of the invention, the above-mentioned emission means emit collimation radiation identical to the radiation from the source for forming an image of the target, in which case only one radiation source is present.

In another particular variant implementation of the invention, the emission means emit collimation radiation which is different from the radiation from the source for forming an image of the target, with the collimation radiation emitted by the emission means preferably being visible radiation while the image-forming radiation emitted by the source is X-radiation.

In another particular implementation of the invention, the collimation radiation is parallel or colinear with the radiation emitted by the source for forming an image of the target, with the collimation radiation emission means including localization means intended to be brought substantially into alignment with at least one of the above-mentioned localization means in each position of the radiation source.

In a particularly advantageous implementation of the invention, the method is applied to the treatment or destruction of the target by shock waves, with the reference point being constituted by a point which is situated on the axis or which coincides with the shock wave focus point that is to be brought into coincidence with the target.

In a particular implementation, the shock wave focus point is constituted by the focusing center of a shock wave generated by any type of generator and focusing equipment, in particular of the magneto-strictive, hydraulic, or electrohydraulic type, in particular constituted by a second focus of a truncated ellipsoid or by a piezoelectric generator and focusing device.

According to another advantageous characteristic of the method of the invention, the radiation receiver device is in a known position relative to the reference point. Advantageously, the center of the receiver device defines the reference point or is situated on an axis of symmetry of the target treatment equipment passing through the reference point.

According to another characteristic of the invention, the above-mentioned localization means and shadow means are disposed on either side of the axis of symmetry of the target treatment equipment passing the reference point.

According to another advantageous characteristic of the invention, a first group of localization means is used, said means being disposed in a horizontal plane of the mask-forming device which is itself perpendicular to the axis of symmetry of the target treatment equipment passing through the reference point, and a second group of localization means is used, said means being disposed in an oblique plane defined by the mask-forming device and forming an angle of known value relative to the horizontal plane containing the first group of localization means of the mask-forming device.

In a second aspect, the present invention also provides an apparatus for determining the exact position of a target relative to a reference point as determined, for example, by equipment for treating the target, the apparatus comprising a radiation emission device comprising a radiation source emitting radiation for forming an image of the target and capable of being received by a radiation receiver device, said source and said receiver device being disposed on opposite sides of said target, wherein the apparatus comprises:

a mask-forming device interposed between the receiver device and the radiation source and comprising at least one localization means of known position relative to the reference point;

means for displacing the radiation emission device in three dimensions, and thus displacing the radiation source between at least two different angular positions;

means being provided for adjusting the orientation in three dimensions of the radiation source relative to the localization means;

means for noting the co-ordinates of two different images of the target resulting from two different angular positions of the source; and means for calculating the co-ordinates of the target on the basis of the noted co-ordinates of the localization means of at least some of the co-ordinates of two different images of the target, and of at least some of the co-ordinates of the first and second images of the localization means as obtained with two different orientations of the source.

A variant embodiment of the apparatus includes means for displacing the mask-forming device out of the beam of radiation for forming an image of the target.

According to another characteristic of the apparatus of the invention, it includes at least one shadow means disposed between the target and the surface of the receiver device to form a shadow, e.g. in the form of a cross, when radiation is emitted for forming an image of the target, said shadow means having co-ordinates which are known relative to the reference point.

Another variant embodiment of the invention includes a first group of localization means and a second group of localization means, said first and second groups of localization means being disposed in two different known angular orientations relative to the reference point.

In another particular embodiment, the first and second groups of localization means are disposed on a frame connected to the reference point, said frame including two substantially plane surfaces, one of which is disposed substantially parallel to the surface of the receiver device and the other of which is disposed sloping at a predetermined known angle relative to the first surface which is parallel to the surface of the receiver device, each surface containing one of said first and second groups of localization means in its plane, and the sloping surface preferably slopes towards the receiver device.

Another particular variant embodiment of the invention includes target treatment equipment determining the reference point with the mask-forming device being connected to the target treatment equipment, and the target may be constituted, in particular, by a cell, by a stone or concretion, or by a bone to be treated.

It will readily be understood that the invention provides all of the above-mentioned technical advantages of significance, together with others that will appear to the person skilled in the art from the following description which is made with reference to the presently preferred implementation of the invention which is given purely by way of example. The scope of the invention is naturally not limited in any way to the specific example.

BRIEF DESCRIPTION OF THE DRAWINGS

An embodiment of the invention is described by way of example with reference to the accompanying drawings, in which.

DETAILED DESCRIPTION

Figure 1:
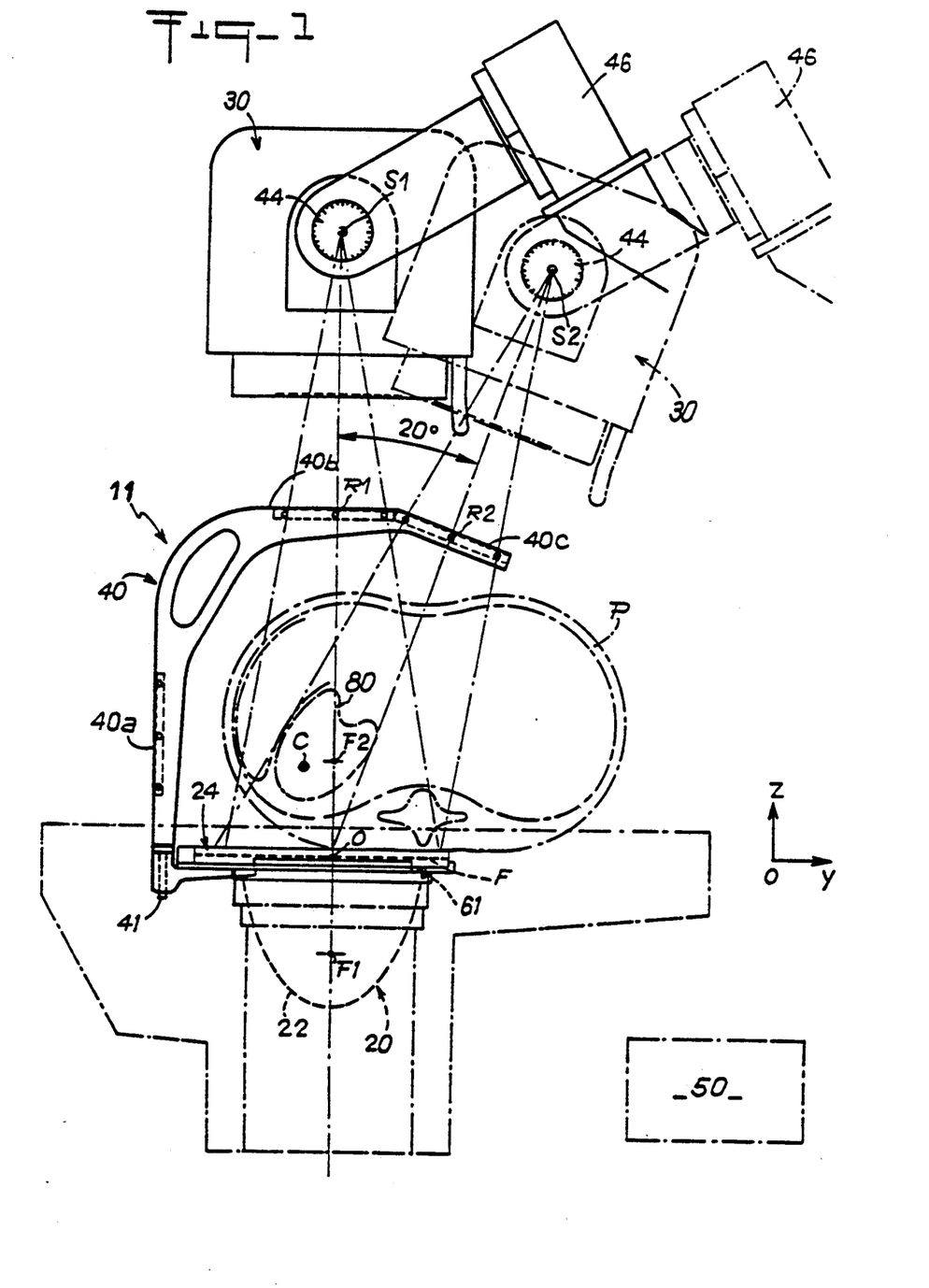
FIG. 1 is a diagrammatic elevation view in a plane perpendicular to a patient P represented by dot-dashed lines, said patient P including a target C to be treated, e.g. a renal concretion or kidney stone, with the view showing the presently preferred embodiment of apparatus of the invention associated with target treatment equipment 20 represented by dashed lines near the bottom of the figure and comprising, for example, a device 22 for generating and focusing shock waves and constituted in conventional manner, for example, by a truncated ellipsoid having an internal focus $F_1$ and an external focus $F_2$.
Figure 2:
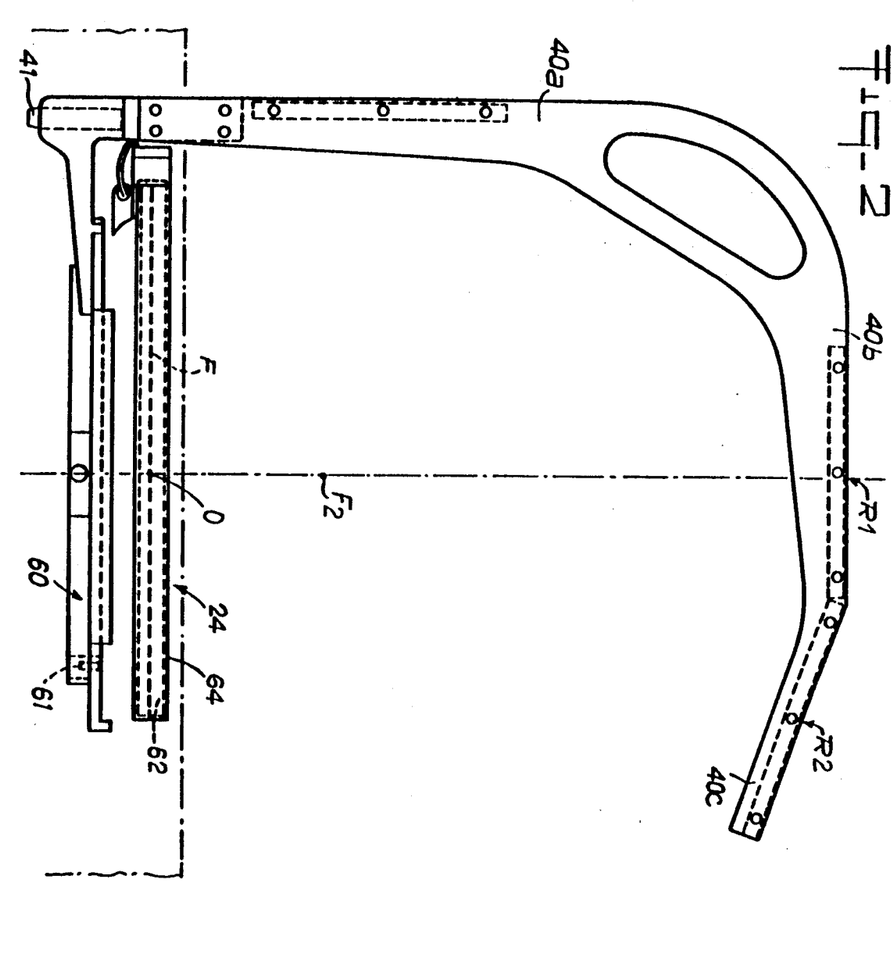
FIG. 2 is a view on a larger scale showing a mask-forming device 40 of the invention which is also visible in FIG. 1.
Figure 2A:
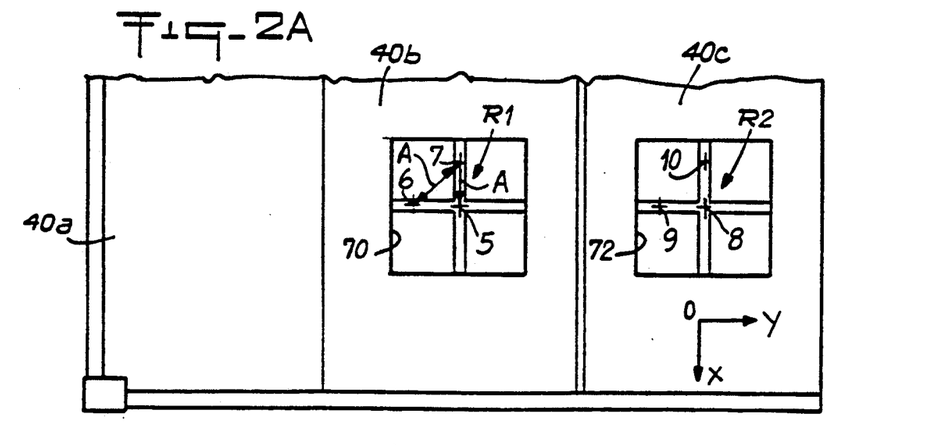
FIG. 2A is a plan view in partial section through the mask-forming device.
Figure 3:
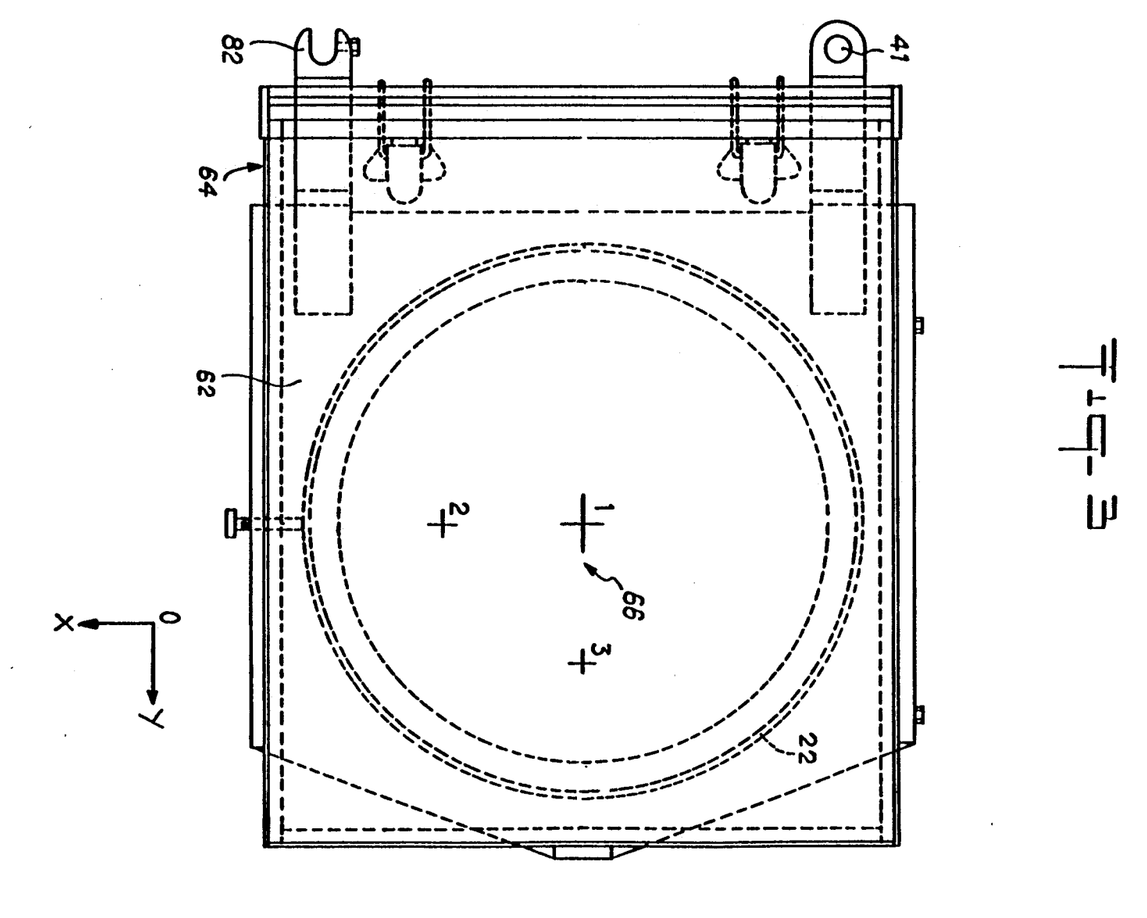
FIG. 3 is a plan view on a larger scale than FIG. 1 showing a particular embodiment of a receiver device 24 for receiving radiation emitted by a radiation source $S_1$, $S_2$ (visible in FIG. 1), this figure having dashed lines showing the position of the target treatment equipment shown in FIG. 1.

With reference to FIGS. 1 to 3, apparatus of the invention is given an overall reference 11. This apparatus serves to determine the exact position of a target C relative to a reference point O as determined, for example, by equipment for treating the target C and designated by overall reference 20.

In FIG. 1, it can be seen that the reference point O is defined by the intersection of the axis of symmetry of the treatment equipment 20 (constituted in this case by a device 22 for generating and focusing shock waves, e.g. a truncated ellipsoid reflector defining an internal focus $F_1$ and an external focus $F_2$ which is to be subsequently brought into coincidence with the target C), and the substantially horizontal plane defined by the surface of a radiation receiver device 24 constituted, for example, by a film F sensitive to the radiation emitted by a source of radiation $S_1$, $S_2$ constituting a part of an emission device given an overall reference 30.

The apparatus of the invention is characterized in that it includes a mask-forming device 40 including at least one group of localization means given overall references $R_1$, $R_2$ of known position relative to the reference point O. In the example shown, the mask-forming device 40 includes a first group of localization means $R_1$ and a second group of localization means $R_2$, with the first and second groups of localization means $R_1$ and $R_2$ being disposed at two different known angular orientations relative to the reference point O, the angular difference being 20°, for example, as shown.

According to a preferred characteristic of the invention, when using two groups of localization means as shown, one ($R_1$) of the first and second groups of localization means $R_1$ and $R_2$ is disposed on the axis of symmetry of the target treatment equipment passing through the reference point O.

The apparatus also includes means for measuring the angular orientation of the radiation source $S_1$, $S_2$ such as a protractor 44 which can be seen in the view of FIG. 1 by way of example and serving to assist the practitioner in positioning the source. Such protractor devices are common practice in conventional radiation-emitting devices 30 and in particular in portable devices as are preferably used in the present case, which devices are independent from the treatment equipment 20. The emission device 30 including the radiation source $S_1$, $S_2$ is thus mounted on a support arm 46 enabling the height of the radiation source $S_1$, $S_2$ to be adjusted and also enabling its angular position in the planes X, Y, and Z to be adjusted, with the support arm itself being mounted on a moving stand (not shown) as is well known in the art.

In addition to its radiation source $S_1$, $S_2$ which is usually an X-ray source, the radiation emission device 30 also includes a source of collimation radiation, which is usually a light source at position $S1'$ and which is disposed in such a manner as to emit radiation which is parallel to or preferably colinear with the X-ray source $S_1$, $S_2$.

In an advantageous embodiment, apparatus of the invention includes calculation means 50 for calculating the co-ordinates of the target C relative to known co-ordinates of the localization means, constituted in this case by the first and second groups of localization means $R_1$ and $R_2$. The calculation is performed on the basis of at least some of the co-ordinates of a first image $I_1$ of the target C using the source $S_1$ and at least some co-ordinates of a second image $I_2$ of the target C using the source $S_2$, together with at least some of the co-ordinates of a first image and a second image of the localization means.

In the presently preferred embodiment of the invention, as shown, the mask-forming device 40 has a section substantially in the form of an upsidedown L-shape, thereby defining a portion 40a which is substantially perpendicular to the plane F and a portion 40b substantially parallel to the plane F. The substantially parallel portion 40b advantageously includes a group of localization means, in this case the group of localization means $R_1$. In the present case, as shown, there are two groups of localization means, with the other localization means $R_2$ being disposed in a plane 40c which is inclined at a predetermined angle relative to the plane of the group of localization means $R_1$, e.g. 20°, and sloping towards the receiver device 24.

In a particular variant embodiment, the mask-forming device 40 may be removably assembled relative to the treatment equipment 20. This may be done, for example, by assembling the mask-forming device 40 on an adapter given overall reference 60 and in a predetermined position relative to the reference point O.

In another particular variant embodiment, the first group of localization means $R_1$ comprises three localization means forming a cross, said means being opaque to X-rays, e.g. by being made of metal, and being given respective references 5, 6, and 7. These reference numbers may also be made of metal and disposed adjacent to the corresponding crosses so as to facilitate visual identification when radiation is projected onto the receiver device. By way of example, the first localization means given reference 5 may be disposed in the center of a window 70 which serves to limit the zone which is exposed to radiation from the radiation source $S_1$ or $S_2$ (generally X-radiation) while the target C is being irradiated by the source $S_1$, $S_2$. Advantageously, the localization means referenced 5 is situated substantially on the axis of symmetry of the treatment equipment 20 as represented by dot-dashed lines in FIG. 2 and as clearly visible in FIG. 1. A second localization means, referenced 6, is at a distance substantially equal to A from the first localization means referenced 5 in a direction extending substantially transversely to the treatment equipment 20 and in the negative Y-axis direction therefrom as can clearly be seen in FIG. 2A. Similarly, the third localization means, referenced 7, is at a distance substantially equal to A from the localization means referenced 5 in a substantially longitudinal direction of the treatment equipment 20 and in the negative X-axis direction, as can also be clearly seen.

The second group of localization means $R_2$ disposed in the oblique plane 40c which slopes at a predetermined angle relative to the plane 40b of the group $R_1$ of localization means is likewise constituted in a preferred embodiment by three X-ray opaque localization means likewise disposed in a window 72 for limiting the zone exposed to radiation. The localization means referenced 8 is disposed in the center of the window 72. The position of the second screen plane 40c is derived from the position of the first screen plane 40b substantially by rotation about an axis situated on the surface of the radiation-sensitive film F (sensitive in particular to X-rays) disposed inside the receiver device 24 as described in greater detail below. This axis passes through the axis of symmetry of the treatment equipment 20 and extends along a substantially longitudinal direction. As a result, the localization means referenced 8, 9, and 10 correspond to the localization means 5, 6, and 7 after such rotation. Similarly, each localization means is accompanied by a reference number made in the form of radiation-opaque metal. It will thus be understood that the localization means referenced 9 is likewise situated in the negative direction along the Y-axis, and the localization means 10 is disposed in the negative direction along the X-axis. It will thus be understood that the position of each of the localization means 5, 6, 7, 8, 9, and 10 is known relative to the treatment equipment 20.

In an advantageous embodiment of the invention, the radiation receiver device 24 is positioned in a predetermined position relative to the adapter 60.

In the example shown, the adapter 60 is removably fixed to the treatment equipment 20, e.g. on the top surface of a truncated ellipsoid reflector 22, and in a predetermined angular position, by means of a position centering point 61 and a countersink engaging one another on the top of the ellipsoid reflector 22.

When the radiation receiver device is constituted by a cassette 62 containing X-ray sensitive film F, it is also advantageous for the cassette 62 to be disposed in a cassette support 64 which is fixed to, or takes up an accurate position relative to, the adapter 60.

As shown in FIG. 3, it is preferable, in accordance with the invention, for the cassette 62 to be provided with a group of shadow means 66 comprising at least one shadow element referenced 1, and preferably three shadow elements as shown (referenced 1, 2, and 3) disposed inside the cassette 62 at a relatively small predetermined distance above the surface of the film F, for the purpose of forming a shadow (e.g. cross shaped) when the source $S_1$ and $S_2$ emits radiation for forming an image of the target C. These cross-shaped shadow means are referenced by metal numbers 1, 2, and 3 for facilitating recognition thereof. The three shadow means 1, 2, and 3 are situated in a plane which is substantially perpendicular to the axis of symmetry of the treatment equipment 20 and they are situated at a known distance from the surface of the film F. Advantageously, the first shadow means referenced 1 is substantially on the axis of symmetry or the main axis, of the treatment equipment 20. The second shadow means referenced 2 lies at a distance substantially equal to 2A where A is equal to 1 inch for example, i.e. 2.54 cm) from the shadow means 1 and substantially in the longitudinal direction of the treatment equipment 20 in the positive X-axis direction, which direction preferably corresponds substantially to the positive X-axis displacement direction of the treatment equipment 20. The third shadow means referenced 3 lies at a distance substantially equal to 2A from the first shadow means 1 in a direction substantially transverse to the displacement direction of the treatment equipment 20 and in the positive Y-axis direction which corresponds substantially to the positive Y-axis displacement direction of the treatment equipment 20.

It can thus be observed that the second and third shadow means referenced 2 and 3 are disposed respectively on the X-axis and on the Y-axis but in the opposite directions to the localization means respectively referenced 7, 10 or 6, 9.

In a variant embodiment, the receiver device 24 for receiving radiation from the source $S_1$ or $S_2$ is in a known fixed position, thereby avoiding the need to use shadow means 66.

Figure 4:
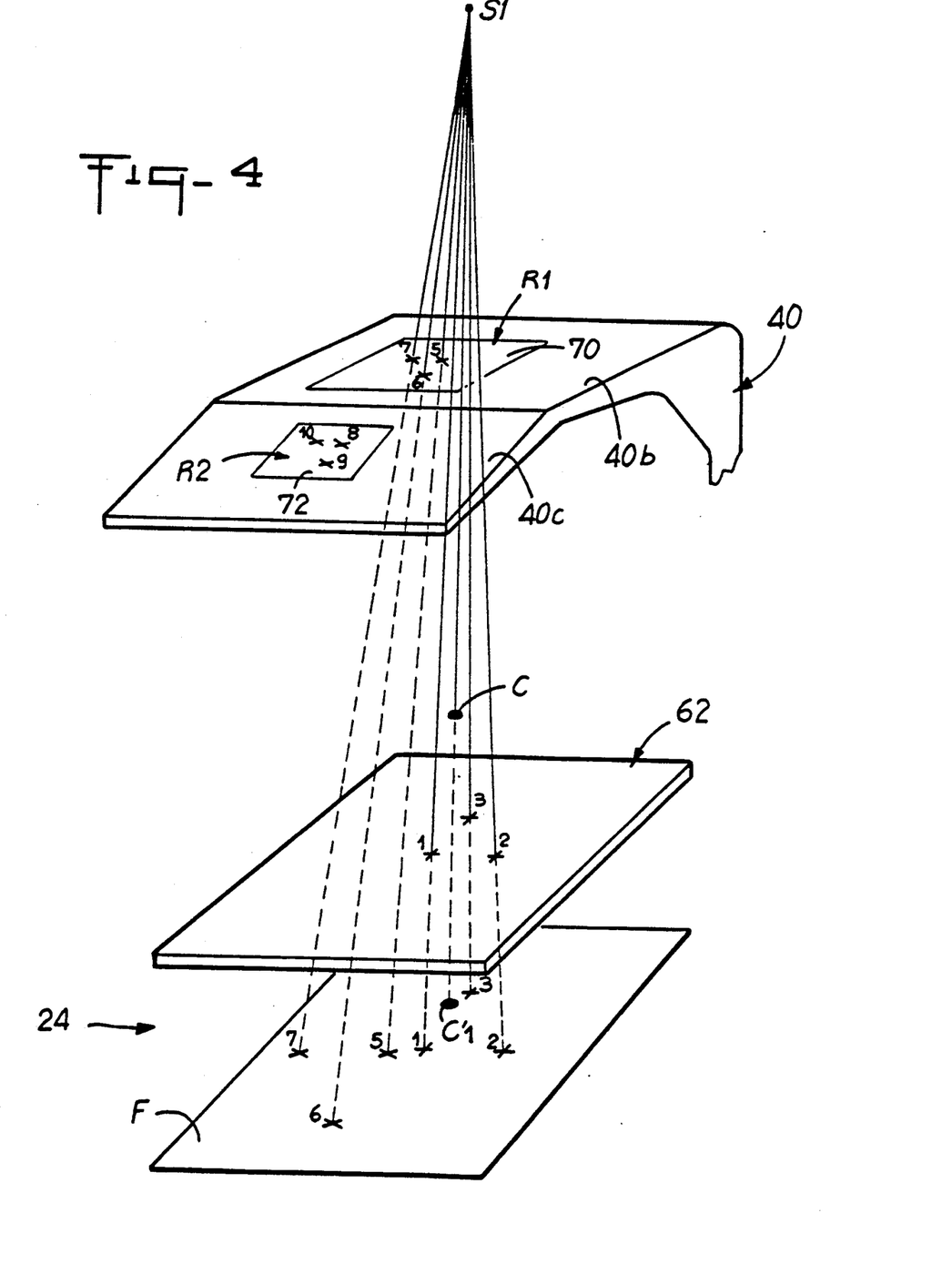
FIG. 4 is a diagrammatic perspective view showing a beam of radiation emitted by the radiation source $S_1$ with the radiation source in a first determined position, e.g. a position which is substantially perpendicular to the surface of the radiation receiver device.
Figure 5:
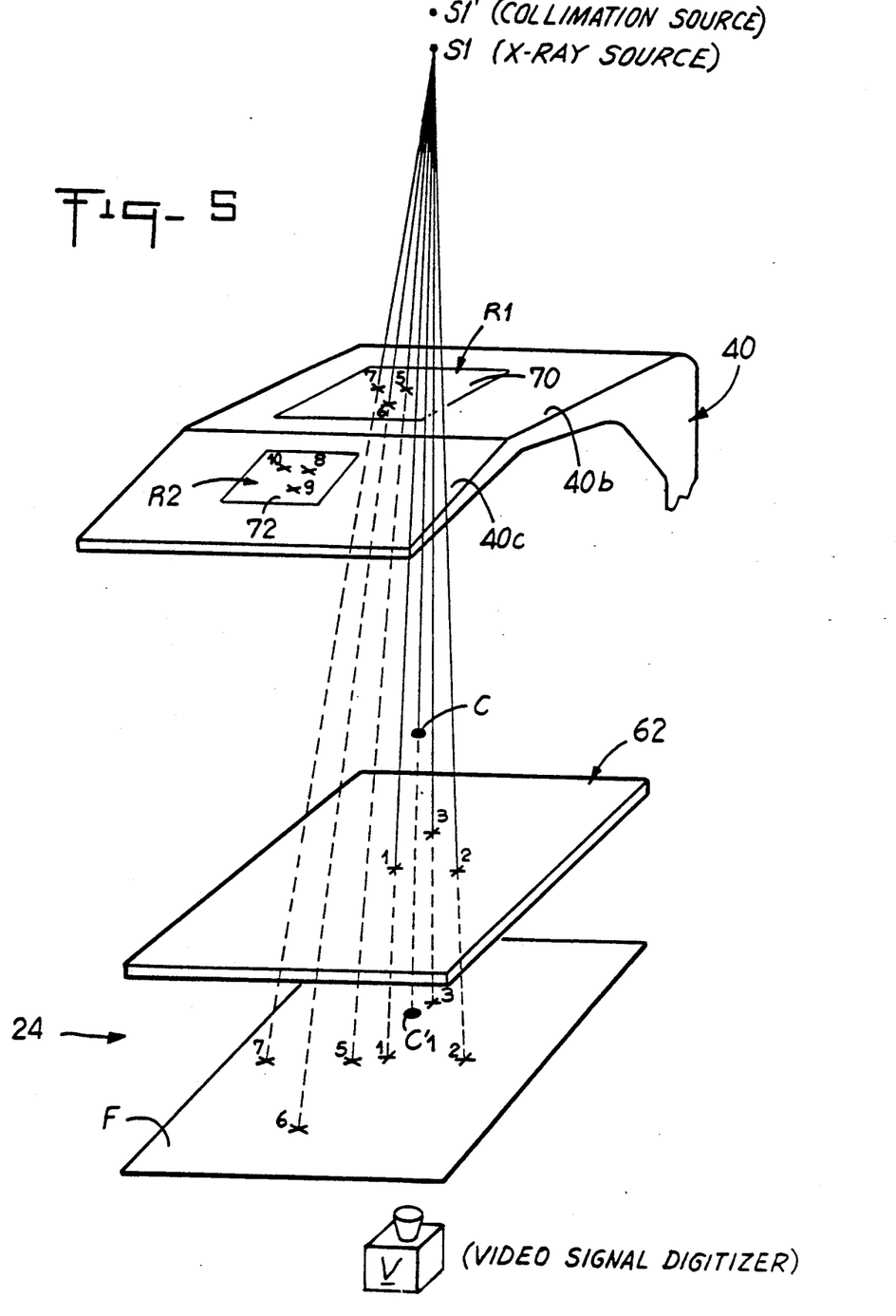
FIG. 5 is a diagrammatic perspective view, showing a video image digitizer V digitizing an image displayed on a fluoroscopic receiver device FL, and a displacable visible light source at position $S1'$ as a collinear collimation radiation source.

FIG. 4 is a diagram showing the members which are essential for determining the position of the target C which may be a kidney stone or a gall bladder stone. These items comprise the source S (shown in its position $S_1$) above the horizontal plane 40b of the mask-forming device 40, and the receiver device 24 which itself comprises a cassette 62 carrying the shadow means 1, 2, and 3, and a sensitive film F onto which the image $C'_1$ or $C'_2$ of the target C is to be projected together with the images of the localization means 5, 6, 7, 8, 9, and 10 and the images of the shadow means 1, 2, and 3. All of the co-ordinates of the localization means and of the shadow means are known, while the co-ordinates of the target C are not known. As shown in FIG. 5, a fluoroscopic device FL may also be used in place of the film F, in which case the thus formed optical image is detected with a device such as a video signal digitizer V.

The operation of apparatus of the invention will readily be understood from the above description. The apparatus of the invention makes it possible to put into operation the method of the invention as defined above. Operation of the apparatus may essentially be defined as follows:

the patient P is initially disposed over the treatment equipment 20 which is itself fitted with the adapter 60 and provided with the radiation receiver device 24, and the radiation source $S_1$ or $S_2$ is put into position above the patient P; and the mask-forming device 40 is interposed between the receiver device 24 (or in this case the patient P) and the radiation source $S_1$ or $S_2$, as shown in FIGS. 1 and 2, with the exact position of the radiation source being unknown or inaccurate in particular because the source is independent from the treatment equipment 20.

It may be observed that this positioning device 40 can be pivotally mounted about an axis 41 which is shown in FIG. 1 and in FIG. 3, thereby facilitating putting it into place by bringing it into abutment against a positioning stop 82 which is fixed to the adapter 60. The device 40 is thus in the form of a frame.

Then, e.g. starting from the position $S_1$ facing the group $R_1$ of localization means 5, 6, and 7 as shown in FIG. 4, it is preferable to emit a light beam from a light source at position S1', which is parallel or collinear with the source for forming an image on the target, an X-ray radiation source at S1, as shown in FIG. 5, integrated in the radiation emission device 30, which beam generally includes a cross-shaped mark, thereby making it possible to bring the mark into alignment with a first localization means such as the means 5 in the group $R_1$, which localization means is likewise in the form of a cross as can clearly be seen in FIG. 2A.

Once alignment has been achieved, it is verified that the light beam encompasses the zone where the target C is assumed to lie, the reference point O, and the film F, and in practice this can be facilitated by preadjusting the corresponding angle on the protractor 44 to a value close to the vertical relative to the substantially horizontal plane of the film F.

The operator causes the treatment equipment 20 to rise until the waterproof cassette 62 is as close as possible to the skin of the patient. This is to minimize attenuation of the X-rays emitted by the radiation source S as they pass through water, with water being used as means for transmitting the treatment waves, e.g. shock waves emitted by the treatment equipment 20 which is constituted, for example, by a shock wave generator and a truncated ellipsoid reflector 22, as is well known to the person skilled in the art. A first exposure to the radiation is thus made by causing the source of radiation S to emit radiation while in its position $S_1$. Advantageously, the position of the treatment equipment 20 while the film F is being exposed may be recorded in a computer. In a variant implementation, the treatment equipment 20 may be lowered to its starting position. The cassette 62 is removed for the purpose of developing the film F, thereby revealing images of the localization means 1, 2, 3, 5, 6, and 7 together with an image $C'_1$ of the stone C. A new waterproof cassette 62 containing X-ray sensitive film is reinserted in the adapter 60.

The moving X-ray apparatus including the source S is then placed over the sloping second plane 40c. The direction in which the radiation source is pointing (now in its position $S_2$ represented in FIG. 1 by dot-dashed lines) is now adjusted so that the main beam is directed substantially along an angle at 20° relative to the vertical so that it is substantially perpendicular to the sloping screen 40c and is directed downwards. The collimation is readjusted, e.g. on the central localization means 8 in the window 72, and a second X-ray exposure is made, with this exposure including the localization means 8, 9, and 10, the target C, and the shadow means 1, 2, and 3. The position of the treatment equipment 20 in which the film is exposed is also recorded in the computer.

When the second film is developed, the images of the points 1, 2, 3, 8, 9, and 10 as well as the image $C'_2$ of the stone C appear on the second film. As shown in FIG. 5, the light source at position S1' is associated with localization means 1', 2', 3', 5', 6' and 7'; when the light source is in a corresponding position to the X-ray apparatus at position S2, it is associated with localization means 1', 2', 3', 8', 9' and 10'. It is easily determined that the displacement of the localization means 1'-10' from localization means 1-10 can be compensated in a known manner. It is preferable for at least each one of corresponding ones of the localization means 5'-7' and 8'-10' to be brought into substantial alignment with the localization means 5-7 and 8-10.

Each of the first and second films can then be placed on a digitizing tablet. The position of the film may be arbitrary, and it can be in any orientation thereon. The only requirements are that the images of the localization points and of the stone should lie over the sensitive zone of the digitizing tablet and that the film should be the right way up. This is easily verified by ensuring that the reference numbers that appear on the film adjacent to the crosses can be read.

In an advantageous implementation, the reference crosses can be pointed to using a stylus or a mouse of appropriate accuracy. A mouse provides greater accuracy. The points successively pointed to with the first film are the points 1, 2, and 3, the stone, and the points 5, 6, and 7, and with the second film they are the points 1, 2, and 3, the stone, and the points 8, 9, and 10.

Each time a point is pointed to, the computer receives X-axis and Y-axis co-ordinate information relative to the point in question.

The computer initially calculates the exact positions in three dimensions of the X-ray source $S_1$ or $S_2$ in each of the two exposures, on the basis both of the data concerning the co-ordinates on the two films of the points pointed to by an operator, and of the positions of the treatment equipment in which the films have been exposed. Thereafter, the position of the stone C is deduced. The mathematical equations describing lines in three dimensions which interconnect the localization points or the stone with the images thereof on the films are well known to the person skilled in the art. These lines necessarily converge on the X-ray source which is assumed to be a point source, thereby giving its position $S_1$ or $S_2$.

It will be understood from the above, that the Z-axis is constituted by the axis of symmetry of the treatment equipment 20, in this case the main axis of the truncated ellipsoid reflector 22, and that the X and Y axes are situated in the plane of the films F. The X-axis extends in the positive X-axis displacement direction of the treatment equipment 20 and substantially in the longitudinal direction of the machine, and the Y-axis extends in the positive Y-axis displacement direction of the machine in a substantially transverse direction.

Further, the positions of the localization points 1 to 3, and 5 to 10 are fixed by design. Their co-ordinates in the working frame of reference are written $x_n$, $y_n$, $z_n$ where n is the number of the point under consideration.

On the basis of the co-ordinates $X_{in}$ and $Y_{in}$ of the points pointed to on the digitizing tablet as expressed in the frame of reference of the tablet, the first procedure is to determine the co-ordinates $x_{in}$, $y_{in}$, and $z_{in}$ of the points in the working frame of reference (where n is the number of the point pointed to, with n=4 corresponding to the stone C, and where i means "image point").

The points pointed to are situated on the surface of the film. Thus, $z_{in}=0$, for all values of n.

$x_{in}$ and $y_{in}$ are determined by changing axes and by changing scale. A scale change consists merely in multiplying the co-ordinates by a scale factor. In order to change axes, a rotation and a translation are required.

The angle of rotation is the angle between the lines interconnecting image points 1-2, 5-7 or 8-10 with the X-axis of the digitizing tablet. It is also the angle between the lines interconnecting image points 1-3, 5-6 or 8-9 with the Y-lines axis of the digitizing tablet. This angle is written α (i.e. the Greek letter "alpha").

$x_{fl}$ and $y_{fl}$ are the co-ordinates of the image of point 1 on the film in the working frame of reference. $x_{fl}$ and $Y_{fl}$ are both unknown a priori. However they are both very close to 0 for the first film and very close to $x=0$ and $y=H1^*\sin 20°$ for the second film, where H1 is the height of the shadow means 1 above the film. Initially they are assumed to be equal to said values.

The axis changing equations are as follows:

$$x_{in}=x_{fl}+((X_{in}-X_{fl})^*\cos\alpha+(Y_{in}-Y_{fl})^*\sin\alpha)^*\text{scale}$$

$$y_{in}=y_{fl}+((X_{in}-X_{fl})^*\cos\alpha+(Y_{in}-Y_{fl})^*\sin\alpha)^*\text{scale}$$

Position of the X-ray source

The co-ordinates of the X-ray source in the vertical position are written $x_{sv}$, $y_{sv}$, and $z_{sv}$ (s for source and v for vertical). The co-ordinates of the source in the oblique position are written $x_{so}$, $y_{so}$, and $z_{so}$ (o for oblique).

The X-ray source during vertical exposure with the first screen lies on the intersection of the straight lines interconnecting the point 5 and its image on the first film, the point 6 and its image on the first film, and the point 7 and its image on the first film.

During the oblique exposure through the second screen, the X-ray source lies on the intersection between the lines joining the point 8 and its image of the second film, the point 9 and its image on the second film, and the point 10 and its image on the second film.

Intermediate calculation variables are written L, L1, and L2. The mathematical equations giving the co-ordinates of the position of the X-ray source in the vertical position are as follows:

$$L1=(x_7-x_5)/(x_{f5}-x_{f7}-x_5+x_7)$$

$$L2=(y_7-y_5)/(y_{f5}-y_{f7}-y_5+y_7)$$

$$L=\tfrac{1}{2}(L1+L2)$$

$$x_{sv}=x_5+L^*(x_{f1}+x_{f5}-x_5)$$

$$y_{sv}=y_5+L^*(y_{f1}+y_{f5}-y_5)$$

$$Z_{sv}=z_5^*(1-L)$$

The mathematical equations giving the co-ordinates of the position of the X-ray source in the oblique exposure are as follows:

$$L1=(x_{10}-x_8)/(x_{f8}-x_{f10}-x_8+x_{10})$$

$$L2=(y_{19}-y_{f8})/(y_8-y_{f1}-y_{f8}-(y_9-y_{f1}-y_{f9})\ ^*z_8/z_9)$$

$$L=\tfrac{1}{2}(1-L1+L2)$$

$$x_{sv}=x_8+(1-L)^*(x_{f1}+x_{f8}-x_8)$$

$$y_{sv}=y_{f1}+y_{f8}-L^*(y_{f1}+y_{f8}-y_8)$$

$$z_{sv}=z_5^*L$$

The results obtained are verified for various consistencies: the source must be situated above the masks ($z>h2$) and the source must be pointing within ±5° about the vertical for the vertical exposure and about 20° for the oblique exposure.

The calculations may be reiterated in order to refine the values for $x_{fl}$ and $y_{fl}$.

Position of the Stone

The stone lies on the intersection of the line joining the source in its vertical position and the image of the stone on the first film and the straight line joining the source in its oblique position and the image of the stone on the second film.

Again there are intermediate calculation variables L1 and L2. The co-ordinates of the image of the stone on the first film are $x_{1v}$, $y_{1v}$, and $z_{1v}$, and the co-ordinates of the image of the stone on the second film are written $x_{1o}$, $y_{1o}$, and $z_{1o}$. Both $z_{1v}$ and $z_{1o}$ are equal to 0.

The mathematical equations for determining the co-ordinates of the stone (X, Y, Z) are as follows:

$$L1=(y_{1o}-y_{so})/(z_{1o}-z_{so})$$

$$L2=(y_{1v}-y_{sv})/(z_{1v}-z_{sv})$$

$$Z=(L1^*z_{so}-L2^*z_{sv}-y_{so}+y_{sv})/(L1-L2)$$

$$X=\tfrac{1}{2}[(x_{1o}-x_{so})^*(z-z_{so})/(z_{1o}-z_{so})+x_{so}$$
$$+(x_{1v}-x_{sv})^*(z-z_{sv})/(z_{1v}-z_{sv})+x_{sv}]$$

This thus provides a method for obtaining the position of the stone in three dimensions relative to a known rectangular frame of reference. The equations given above are given by way of example and in particular they take advantage of the special situation of the localization points. These equations are reduced from a system of general equations for determining the position of a stone while using localization points that are disposed arbitrarily.

It will thus be understood that the present invention makes it possible to calculate the position in three dimensions of the target C very accurately, thereby making it possible to obtain extremely reliable and reproducible treatment of the target C and this is particularly important when applying therapy, e.g. when treating kidney stones or lithiasis present in the kidney 80 of a patient P or in the treatment of bone tumors, by using shock waves emitted by a shock wave generator device 20, in a manner well known to the person skilled in the art.

When using an X-ray emitting source $S_1$ or $S_2$, in combination with a receiver device 24 including an X-ray sensitive film F, the present invention makes it possible to avoid the need for a priori knowledge about the position of the source, thereby making it possible to use any radiation device 30 that may be available in a treatment center, and in particular making it possible to use moving devices.

Further, the invention makes it possible to subject patients to minimum doses of radiation without any need to modify the patient treatment equipment significantly, since all that is required is an additional mask-forming device 40 used in association with a cassette system containing the film F, which system is itself conventional, or else in association with a fluoroscopic device FL, as is also conventional. It is also necessary to use a system for measuring cartesian co-ordinates, e.g. in the form of a digitizing tablet or in the form of a system for digitizing a video signal, both of which are conventional.

Further, the invention makes it possible to perform the above method without displacing the patient, and while exposing the patient only twice to X-rays, whereas prior apparatuses have required a much larger number of exposures prior to determining the exact position of the target.

We claim:

1. A method of determining the position of a target relative to a reference point of a target treatment equipment, comprising the steps of:

emitting radiation from an X-ray source freely movable relative to said target treatment equipment and of unknown position relative thereto for forming an X-ray image of the target, the X-ray radiation being received by an X-ray receiver device of known position relative to said reference point, the X-ray source and X-ray receiver device being disposed on opposite sides of the target, said X-ray source being freely movable and of unknown position relative to said X-ray receiver;

disposing a mask-forming device between the receiver device and the X-ray source, the mask-forming device comprising at least one group of X-ray opaque localization means of known position coordinates relative to said reference point;

positioning the S-R source into a first unknown position relative to said target treatment equipment for which the XR radiation emitted by the XR source simultaneously encompasses the XR receiver device, the target and said at least one group of localization means;

emitting a first quantity of X-ray radiation from the X-ray source to form a first X-ray image of the target and the at least one group of localization means on the X-ray receiver device, and determining the respective first image position coordinates thereof in said first X-ray image;

calculating the position coordinates of the target on the basis of the known position coordinates of the at least one group of localization means, and at least some of the first image position coordinates of the at least one group of localization means and the target.

2. The method of claim 1, wherein said X-ray receiver device comprises an X-ray film and a holder for said film, said holder being of known position relative to said reference point and said film being of unknown X-ray relative to said reference point, said holder incorporating an opaque shadow means of known position coordinates relative to the reference point and encompassed by said X-ray source in said first position for forming an image of said shadow means on said film; and wherein said step of calculating the position coordinates of the target further comprises calculating the position coordinates of the target on the basis of at least some of the known position coordinates of the shadow means.

3. The method of claim 2, and further comprising the step of determining the first image position coordinates of said shadow means on said film, and wherein said step of calculating the position coordinates of said target further comprises calculating the position coordinates of the target on the basis of at least some of the first image position coordinates of said shadow means.

4. The method of claim 1, further comprising the steps of:

displacing the X-ray source to a second unknown position relative to said target treatment equipment which is different from the first unknown position, the X-ray radiation in the second position simultaneously encompassing the X-ray receiver device, the target, and said at least one group of localization means;

emitting a second quantity of X-ray radiation from the X-ray source to form a second X-ray image of the target and the at least one group of localization means on the X-ray receiver device, and determining respective second image position coordinates thereof in said second X-ray image; and wherein said step of calculating the position coordinates of the target further comprises calculating the position coordinates of the target based on at least some of the second image position coordinates of the at least one group of localization means and the target.

5. The method of claim 4, wherein said step of disposing a mask-forming device comprises disposing a mask forming device having two non-coplanar surfaces, said at least one group of localization means comprising a first group of X-ray opaque localization means in one of said two non-coplanar surfaces and a second group of X-ray opaque localization means in the other of said two non-coplanar surfaces;

wherein said step of positioning the X-ray source into a first unknown position comprises positioning the X-ray source to encompass the first group of localization means;

wherein said step of displacing the X-ray source to a second unknown position comprises displacing said X-ray source to a second position encompassing said second group of localization means; and wherein said step of calculating the position coordinates of the target further comprises calculating the position coordinates of the target on the basis of the known coordinates of the first and second groups of localization means and at least some of the first and second image position coordinates, respectively, of said first and second groups of localization means.

6. The method of claim 5, wherein said step of positioning said X-ray source into a first unknown position comprises positioning said X-ray source into a position wherein said X-ray radiation is substantially perpendicular to said one of said two non-coplanar surfaces, and said step of displacing said X-ray source to a second unknown position comprises displacing said X-ray source to a position wherein said X-ray radiation is substantially perpendicular to the other of said two non-coplanar surfaces.

7. The method of claim 4, wherein said X-ray receiver device comprises an X-ray film and a holder for said film, said holder being of known position relative to said reference point and said film being of unknown position relative to said reference point, said holder incorporating an opaque shadow means of known position coordinates relative to the reference point and encompassed by said X-ray source in said first and second positions for forming images of said shadow means on said film in said first and second X-ray images; and wherein said step of calculating the position coordinates of the target further comprises calculating the position coordinates of the target on the basis of at least some of the known position coordinates of the shadow means.

8. The method of claim 7, and further comprising the step of determining the first and second image position coordinates of said shadow means on said film, and wherein said step of calculating the position coordinates of said target further comprises calculating the position coordinates of the target on the basis of at least some of the first and second image position coordinates of said shadow means.

9. An apparatus for determining the position of a target relative to a reference point of a target treatment equipment, comprising:

an X-ray source for emitting radiation freely movable relative to said target treatment equipment and of unknown position relative thereto for forming an X-ray image of the target, an X-ray receiver device for receiving X-ray radiation, said X-ray receiver device being of known position relative to said reference point, the X-ray source and X-ray receiver device being disposed on opposite sides of the target, said X-ray source being freely movable and of unknown position relative to said X-ray receiver;

a mask-forming device disposed between the receiver device and the X-ray source, the mask-forming device comprising at least one group of X-ray opaque localization means of known position coordinates relative to said reference point;

positioning means for positioning the X-ray source into a first unknown position relative to said target treatment equipment for which the X-ray radiation emitted by the X-ray source simultaneously encompasses the X-ray receiver device, the target and said at least one group of localization means, said X-ray source in said first unknown position emitting a first quantity of X-ray radiation to form a first X-ray image of the target and the at least one group of localization means on the X-ray receiver device;

determining means for determining the respective first image position coordinates of the target and the at least one group of localization means in said first X-ray image;

calculating means for calculating the position coordinates of the target on the basis of the known position coordinates of the at least one group of localization means, and at least some of the first image position coordinates of the at least one group of localization means and the target.

10. The apparatus of claim 9, wherein said X-ray receiver device comprises an X-ray film and a holder for said film, said holder being of known position relative to said reference point and said film being of unknown position relative to said reference point, said holder incorporating an opaque shadow means of known position coordinates relative to the reference point and encompassed by said X-ray source in said first position for forming an image of said shadow means on said film; and wherein said calculating means comprises means for calculating the position coordinates of the target on the basis of at least some of the known position coordinates of the shadow means.

11. The apparatus of claim 10, wherein said determining means further comprises means for determining the first image position coordinates of said shadow means on said film, and wherein said calculating means further comprises means for calculating the position coordinates of said target on the basis of at least some of the first image position coordinates of said shadow means.

12. The apparatus of claim 9, further comprising:

displacing means for the X-ray source to a second unknown position relative to said target treatment equipment which is different from the first unknown position, the X-ray radiation in the second position simultaneously encompassing the X-ray receiver device, the target, and said a least one group of localization means, said X-ray source in said second unknown position emitting a second quantity of X-ray radiation from the X-ray source to form a second X-ray image of the target and the at least one group of localization means on the X-ray receiver device;

wherein said determining means comprises means for determining respective second image position coordinates thereof in said second X-ray image; and wherein said calculating means comprises means for calculating the position coordinates of the target based on at least some of the second image position coordinates of the at least one group of localization means and the target.

13. The apparatus of claim 12, wherein said mask-forming device comprises a mask forming device having two non-coplanar surfaces, said at least one group of localization means comprising a first group of X-ray opaque localization means in one of said two non-coplanar surfaces and a second group of X-ray opaque localization means in the other of said two non-coplanar surfaces;

wherein said positioning means comprises means for positioning the X-ray source in a first unknown position encompassing the first group of localization means;

wherein said displacing means comprises means for displacing the X-ray source to a second unknown position encompassing said second group of localization means; and wherein said calculating means comprises means for calculating the position coordinates of the target on the basis of the known coordinates of the first and second groups of localization means and at least some of the first and second image position coordinates, respectively, of said first and second groups of localization means.

14. The apparatus of claim 13, wherein said positioning means comprises means for positioning said X-ray source into a first unknown position comprises positioning said X-ray source into a position wherein said X-ray radiation is substantially perpendicular to said one of said two non-coplanar surfaces, and wherein said displacing means comprises means for displacing said X-ray source to a second unknown position wherein said X-ray radiation is substantially perpendicular to the other of said two non-coplanar surfaces.

15. The apparatus of claim 12, wherein said X-ray receiver device comprises an X-ray film and a holder for said film, said holder being of known position relative to said reference point and said film being of unknown position relative to said reference point, said holder incorporating an opaque shadow means of known position coordinates relative to the reference point and encompassed by said X-ray source in said first and second positions for forming, respectively, first and second images of said shadow means on said film in said first and second X-ray images; and wherein said calculating means comprises means for calculating the position coordinates of the target on the basis of at least some of the known position coordinates of the shadow means.

16. The apparatus of claim 15, wherein said determining means further comprises means for determining the first and second image position coordinates of said shadow means on said film, and wherein said calculating means comprises means for calculating the position coordinates of said target on the basis of at least some of the first and second image position coordinates of said shadow means.

17. A target positioning device for use with a target treatment equipment for treating a target in a portion of a patient's body, comprising:
- a frame member locatable in a known position relative to target treatment equipment;
- an X-ray receiver device secured to said frame for receiving X-ray radiation emitted by an X-ray source; and
- at least one group of X-ray opaque localization means secured to said frame and disposed in non-coplanar relation with said X-ray receiver and sufficiently spaced apart therefrom to accommodate disposition of said portion of said patient's body therebetween, whereby X-ray radiation emitted by said X-ray source encompasses said target, said X-ray opaque localization means and said X-ray receiver device.

18. The device of claim 17, wherein said at least one group of X-ray opaque localization means comprises at least two groups of X-ray opaque localization means disposed in non-coplanar relation with said X-ray receiver device;
- whereby in a first position of said X-ray source X-ray radiation emitted by said X-ray source encompasses said target, said first group of X-ray opaque localization means and said X-ray receiver device, and in a second position of said X-ray source X-ray radiation emitted by said X-ray source encompasses said target, said second group of X-ray opaque localization means and said X-ray receiver source.

19. The device of claim 17, wherein said X-ray receiver device is releasably secured to said frame.

20. The device of claim 17, wherein said frame further comprises an opaque shadow means located in a known position relative to said target treatment equipment for projecting an image on said X-ray receiver device for establishing the position of the X-ray receiver device relative to the target treatment equipment, whereby X-ray radiation emitted by said X-ray source encompasses said target, said X-ray opaque localization means, said opaque shadow means and said X-ray receiver device.

21. The device of claim 20, wherein said X-ray receiver device comprises a holder and a film received in said holder for receiving said X-ray radiation, and wherein said frame further comprises shadow means located in a known position relative to said target treatment equipment.

22. The device of claim 21, wherein said shadow means is incorporated in said holder.

23. A method of determining the exact position of a target relative to a reference point of target treatment equipment, comprising the steps of:
- emitting radiation from an X-ray source freely movable relative to said treatment equipment and of unknown position relative thereto for forming an X-ray image of the target, the X-ray radiation being received by an X-ray receiver device, the X-ray source and the X-ray receiver device being disposed on opposite sides of the target with said X-ray source being freely movable and of unknown position relative to said X-ray receiver device, said X-ray receiver device being of known position relative to said reference point of said target treatment equipment;
- disposing a mask-forming device between the receiver device and the X-ray source, the mask-forming device comprising at least one group of X-ray opaque localization means of known position relative to the reference point,
- positioning the X-ray source into a first unknown position relative to said target treatment equipment for which the X-ray radiation emitted by the X-ray source simultaneously encompasses the X-ray receiver device, the target, and at least one group of localization means;
- emitting a first quantity of X-ray radiation from the X-ray source to form a first X-ray image of the target and a first X-ray image of the localization means on the X-ray receiver device, and determining the respective first position coordinates thereof in said first X-ray image;
- displacing the X-ray source to a second unknown position relative to said target treatment equipment which is different from the first unknown position, the X-ray radiation emitted by the X-ray source in the second position simultaneously encompassing the X-ray receiver device, the target, and at least one group of localization means;
- emitting a second quantity of X-ray radiation from the X-ray source to form a second X-ray image of the target and a second X-ray image of the localization means on the X-ray receiver device, and determining respective second position coordinates thereof in said second X-ray image; and
- calculating the coordinates of the target on the basis of the known coordinates of the at least one group of localization means, and of at least some of the first and second position coordinates of the target and the localization means.

24. A method according to claim 23, wherein the mask-forming device comprises a first group of localization means and a second group of localization means each having known position relative to the reference point, and further comprising the steps of:
- disposing the first and second groups of localization means at two different known angular orientations relative to the reference point;
- irradiating a first of the at least one group of localization means in the first image and a second of the at least one group of localization means in the second image; and
- calculating the coordinates of the target on the basis of the known coordinates of the first and second groups of localization means, and of at least some of the first and second position coordinates of the target and the localization means.

25. A method according to claim 23, further comprising the steps of providing a first group of at least three localization means each having known coordinates and disposing the at least three localization means in a given plane, and providing a second group of at least three localization means of known coordinates disposed in a common oblique plane sloping at a known angle relative to the first group of localization means.

26. A method according to claim 23, further comprising the steps of disposing the localization means and the reference point on an axis of symmetry of the target treatment equipment.

27. A method according to claim 26, further comprising the step of disposing the plane of the first group of localization means substantially perpendicular tot he axis of symmetry of the treatment equipment.

28. A method according to claim 23, further comprising the step of disposing at least one shadow means having known coordinates relative to the reference point between the target and the receiver device to form a shadow on the receiver device while simultaneously emitting image-forming radiation through the target toward the receiver.

29. A method according to claim 28, further comprising the steps of providing a plurality of shadow means and disposing the shadow means on the receiver device in a plane perpendicular to an axis of symmetry of the treatment equipment.

30. A method according to claim 23, wherein the receiver is an X-ray sensitive film, said emitting step further comprising measuring at least some of the coordinates of the first and second images of the target and of at least some of the coordinates of the first and second images of the localization means formed on the X-ray sensitive film with a system for measuring cartesian coordinates.

31. A method according to claim 23, wherein the receiver is a fluoroscopic receiver device having a monitor screen, said emitting step further comprising measuring at least some of the coordinates of the first and second images of the target and of at least some of the coordinates of the first and second images of the localization means formed on the fluoroscopic receiver with a system for digitizing a video signal including a system measuring cartesian coordinates.

32. A method according to claim 23, further comprising the step of emitting a beam of collimation X-ray identical to the image-forming X-ray from the radiation source for aligning the emission device with the reference point.

33. A method according to claim 23, further comprising the step of emitting a beam of visible collimation radiation for aligning the X-ray source with the reference point.

34. A method according to claim 23, further comprising the steps of:
emitting a beam of collimation radiation which is collinear with image-forming X-ray emitted by the X-ray source; and
aligning the collimation radiation with at least one of the groups of localization means for each position of the X-ray source.

35. A method according to claim 23, wherein the reference point is a focus point or a point along an axis of symmetry of a shockwave treatment apparatus, further comprising the step of aligning the shockwave focus point with the target.

36. A method according to claim 35, wherein the shockwave focus point is an external focus point of a truncated ellipsoid having a magnetostrictive, hydraulic or electro-hydraulic shock wave generator of a focus point of a piezoelectric generator with a focusing device, further comprising the step of determining the shockwave focus point of the shockwave treatment apparatus.

37. The method according to claim 23, wherein the radiation source in the first position is between −5° and +5° from an axis of symmetry of the treatment apparatus, and the radiation source in the second position is about 20° from the axis of symmetry.

38. A method according to claim 23, wherein the apparatus further comprises an adaptor for removably installing the mask-forming device, further comprising the step of removing the mask-forming device from the treatment equipment after the second image is received by the receiving device.

39. A method according to claim 23, wherein the apparatus further comprises a pivot for mounting the mask-forming device relative to the treatment equipment, comprising the further step of pivoting the mask relative to the treatment equipment at the pivot.

40. Apparatus for determining the exact position of a target relative to a reference point of equipment for treating the target, the apparatus including an external X-ray source freely movable relative to said treating equipment and of known position relative thereto for emitting radiation for forming an X-ray image of the target, and an X-ray receiver device for receiving X-ray radiation from said X-ray source, the X-ray source and the X-ray receiver device being disposed on opposite sides of the target, with said X-ray source being freely movable and of unknown position relative to said X-ray receiver device, said receiver device being of known position relative to said reference point, said apparatus comprising:
a mask-forming device interposed between the X-ray receiver device and the X-ray source and comprising at least one group of X-ray opaque localization means of known position relative to the reference point;
means for displacing the X-ray source in space between at least first and second different unknown positions relative to said target treating equipment for forming first and second images, respectively, of said target and said at least one group of localization means;
determining means for determining, respectively, first and second position coordinates in said first and second X-ray images of the target and the at least one group of localization means; and
calculating means for calculating the coordinates of the target on the basis of the known position of the at least one group of localization means, and of at least some of the first and second position coordinates of the target and said localization means.

41. The apparatus according to claim 40, further comprising means for displacing the mask-forming device out of a beam of radiation for forming an image of the target.

42. The apparatus according to claim 40, further comprising target treatment equipment associated with the reference point, said mask-forming device being connected to the target treatment equipment.

43. The apparatus according to claim 42, wherein the treatment equipment is a device selected from the group consisting of magnetostrictive, hydraulic, or electrohydraulic equipment for generating and focusing shock waves at a focal point of a truncated ellipsoidal generator or a piezoelectric generator and focusing device having a focus point, said focus point being displaceable with respect to the target so that they may be made coincident.

44. The apparatus according to claim 40, wherein the target treatment has an axis of symmetry and one of the localization means as well as the reference point are both disposed on an axis of symmetry.

45. The apparatus according to claim 40, further comprising at least one shadow means disposed between the target and the surface of the receiver device for forming a shadow of attenuated radiation having features along at least two axes when radiation is emitted for forming an image of the target, said shadow means having predetermined coordinates relative to the reference point.

46. The apparatus according to claim 40, further comprising a first group of localization means and a second group of localization means, said first and second groups of localization means being disposed in two different predetermined angular orientations relative to the reference point.

47. The apparatus according to claim 46, wherein the first and second groups of localization means are disposed on portions of said mask-forming device, said mask-forming device comprising a frame connected to said receiver device, said frame including at least two substantially planar surfaces, one of which is mounted parallel to the surface of the receiver device and the other being mounted at a predetermined angle relative to the receiver device, each said planar surface containing either said first or said second groups of localization means in its plane.

48. In an apparatus for determining the exact position of a target relative to a reference point of equipment for treating the target, the apparatus including an external X-ray source freely movable relative to said treating equipment and of unknown position relative thereto for emitting radiation for forming an X-ray image of the target, said X-ray radiation being received by an X-ray receiver device, the X-ray source and the X-ray receiver device being disposed on opposite sides of the target with said X-ray source being freely movable and of unknown position relative to said X-ray receiver device, means for positioning the X-ray source in space between at least first and second different unknown positions relative to the equipment for treating the target for forming first and second X-ray images of the target, and means for measuring the coordinates of said target in said first and second X-ray images, the improvement comprising:

said X-ray receiver device being of known position relative to said reference point of said target treatment equipment;

a mask-forming device interposed between the X-ray receiver device and the X-ray source and comprising at last one X-ray opaque localization means of known position coordinates relative to the reference point, whereby said first and second X-ray images of said target include, respectively, first and second X-ray images of said localization means;

said means for measuring further comprising means for measuring the coordinates of the localization means relative to the reference point in said first and second X-ray images; and means for calculating the position coordinates of the target on the basis of said known position coordinates of the localization means, and of at least some of said measured coordinates of the localization means and the target in said first and second X-ray images.

49. The apparatus according to claim 48, further comprising a first group of localization means and a second group of localization means, said first and second groups of localization means being disposed in two different predetermined angular orientations relative to the reference point.

50. The apparatus according to claim 48, further comprising means for displacing the mask-forming device out of a beam of X-rays emitted by said X-ray source for forming an image of the target.

51. The apparatus according to claim 50, further comprising:

means for pivotally mounting said mask-forming device for pivotal movement relative to the X-ray receiver device; and an adapter means for releasably securing said mask-forming device to said X-ray receiver device.

52. The apparatus according to claim 51, wherein the first and second groups of localization means are disposed on said mask-forming device, said mask-forming device comprising a frame connected by an adapter to said X-ray receiver device, said frame including at least two substantially planar surfaces, one of said planar surfaces being mounted substantially parallel to the surface of the X-ray receiver device and the other of said planar surfaces being mounted at a predetermined angle relative to the X-ray receiver device, each of said planar surfaces containing one of said first and said second groups of localization means.

53. The apparatus according to claim 52, wherein said frame means includes a third substantially planar member disposed perpendicularly to the surface of the receiver device.

* * * * *